United States Patent [19]

VandenBerg

[11] Patent Number: Plant 6,900

[45] Date of Patent: Jul. 4, 1989

[54] CHRYSANTHEMUM PLANT NAMED APTO

[75] Inventor: Cornelis P. VandenBerg, Salinas, Calif.

[73] Assignee: Yoder Brothers, Inc., Ashtabula, Ohio

[21] Appl. No.: 187,577

[22] Filed: Apr. 28, 1988

[51] Int. Cl.[4] ..... A01H 5/00
[52] U.S. Cl. ..... Plt./74
[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Apto particularly characterized by its flat capitulum form; daisy capitulum type; purple ray floret color; diameter across face of capitulum of up to 10 cm at maturity; uniform nine week photoperiodic flowering response to short days; peduncle length ranging from 10 to 20 cm on open, terminal sprays; short plant height when grown as a single stem spray cut mum; and excellent tolerance to high temperatures for bud initiation and flower development.

3 Drawing Sheets

The present invention comprises a new and distinct cultivar of Chrysanthemum, botanically known as *Dendranthema grandiflora,* and referred to by the cultivar name Apto.

Apto, identified as 84244015, was originated from a cross made by Cornelis P. VandenBerg in a controlled breeding program in Salinas, Calif. in 1984.

The female parent and the male parent of Apto were both unnamed seedlings, identified respectively as 78546013 and 79T69011.

Apto was discovered and selected as one flowering plant within the progeny of the stated cross by Cornelis P. VandenBerg in December 1984 in a controlled environment in Salinas, Calif.

The first act of asexual reproduction of Apto was accomplished when vegetative cuttings were taken from the initial selection in February 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Apto are firmly fixed and are retained through successive generations of asexual reproduction.

Apto has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The high temperature tolerance was determined in repeated summer flowerings in Louisville, Ky., and in Italy.

The following traits have been repeatedly observed and are determined to be basic characteristics of Apto, which, in combination, distinguish this Chrysanthemum as a new and distinct cultivar:

1. Flat capitulum form.
2. Daisy capitulum type.
3. Purple ray floret color.
4. Diameter across face of capitulum up to 10 cm at maturity.

5. Uniform nine week photoperiodic flowering response to short days.
6. Peduncle length ranging from 10 to 20 cm on open terminal sprays.
7. Short plant height, requiring 2 to 3 long day weeks prior to short days to attain a flowered plant height of 90 to 100 cm for year-round flowerings.
8. Excellent tolerance to high temperatures for bud initiation and flower development.

The accompanying photographic drawings show typical inflorescence and leaf characteristics of Apto, with the colors being as nearly true as possible with illustrations of this type.

Sheet 1 is a color photograph of Apto grown as a single stem cut spray mum.

Sheet 2 is a black and white photograph of three views of the inflorescence of Apto.

Sheet 3 is a black and white photograph showing the upper and under sides of the leaves of Apto at three stages of development (mature, intermediate and immature).

Of the commercial cultivars known to the inventor, the most similar in comparison to Apto is Brioso, disclosed in the inventor's pending Plant patent application, Ser. No. 049,779. Reference is made to Chart A, which compares certain characteristics of Apto to the same characteristics of Brioso. Similar traits are color of ray florets, with Brioso being slightly darker than Apto, capitulum form and type, and flowering response. Apto has a more semi-upright spray formation, the diameter of capitulum is smaller, and high temperature tolerance is better than Brioso. Apto requires more long days than Brioso to attain a plant height of 90 to 100 cm.

In the following description, color references are made to The Royal Horticultural Society Colour Chart. The color values were determined on plant material grown in Salinas, Calif. on Oct. 14, 1987.

Classification:

*Botanical.*—*Dendranthema grandiflora,* cv Apto.
*Commercial.*—Daisy cut spray mum.

INFLORESCENCE

A. Capitulum:

*Form.*—Flat.
*Type.*—Daisy.
*Diameter across face.*—Up to 10 cm at maturity.

B. Corolla of ray florets:
*Color (general tonality from a distance of three meters).*—Purple.
*Color (upper surface).*—75A to 75B.
*Color (under surface).*—75B.
*Shape.*—Flat, narrow, slightly pointed.

C. Corolla of disc florets:
*Color (mature).*—Closest to 7A.
*Color (immature).*—Closest to 144B.

D. Reproductive organs:
*Androecium:*—Present on disc florets only; scant pollen.
*Gynoecium.*—Present on both ray and disc florets.

PLANT

A. General appearance:
*Height.*—Short; 90 to 100 cm as a single stem cut mum with 2 to 3 long day weeks prior to short days.

B. Foliage:
*Color (upper surface).*—147A.
*Color (under surface).*—147B.

*Shape.*—Deeply lobed and sharply serrated.

CHART A

COMPARISON OF APTO AND BRIOSO

| | Apto | Brioso |
|---|---|---|
| Ray floret color | Purple | Purple |
| Capitulum form and type | Flat<br>Daisy | Flat<br>Daisy |
| Spray formation | Semi-upright<br>Terminal<br>10 to 20 cm peduncles | Wide<br>Terminal<br>10 to 25 cm peduncles |
| Diameter across face of capitulum | Up to 10 cm | Up to 125 mm |
| Plant height | Short | Tall |
| Flowering response period | 9 weeks | 9 weeks |
| High temperature tolerance | Excellent | Good |

COMPARISONS MADE OF PLANTS GROWN AS SINGLE STEM SPRAY CUT MUMS IN SALINAS, CALIFORNIA

I claim:

1. A new and distinct Chrysanthemum plant named Apto, as described and illustrated, and parts thereof.

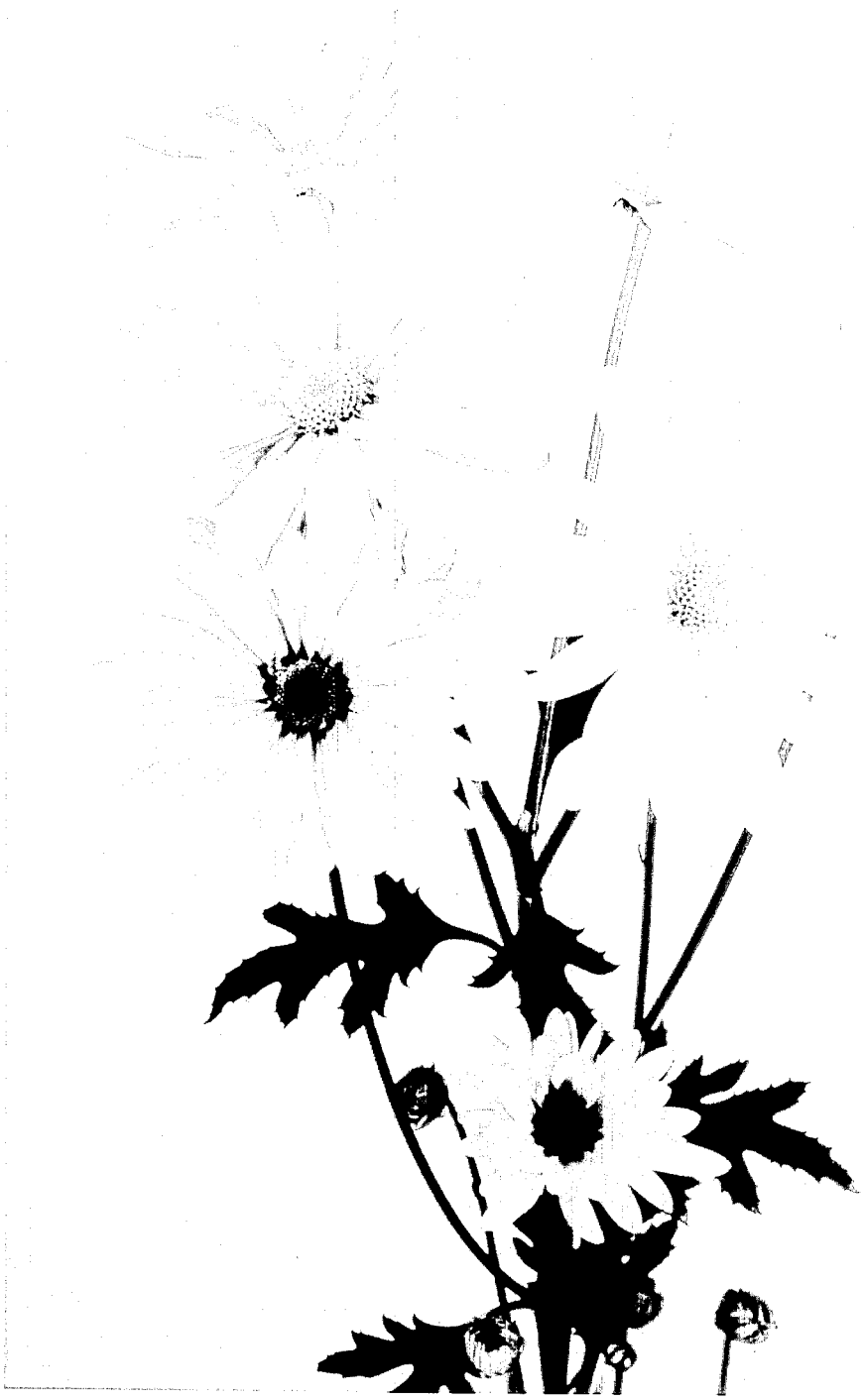

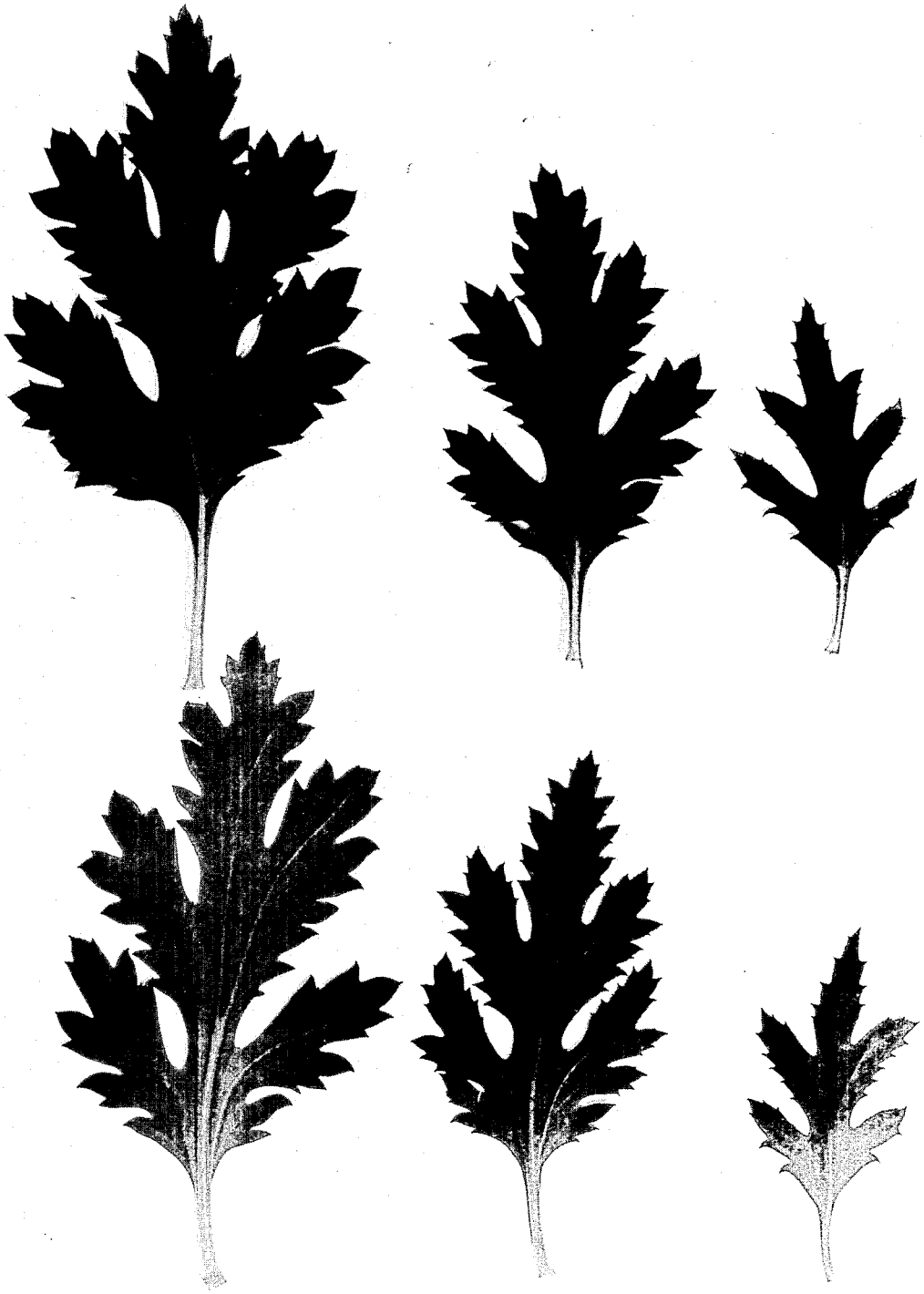

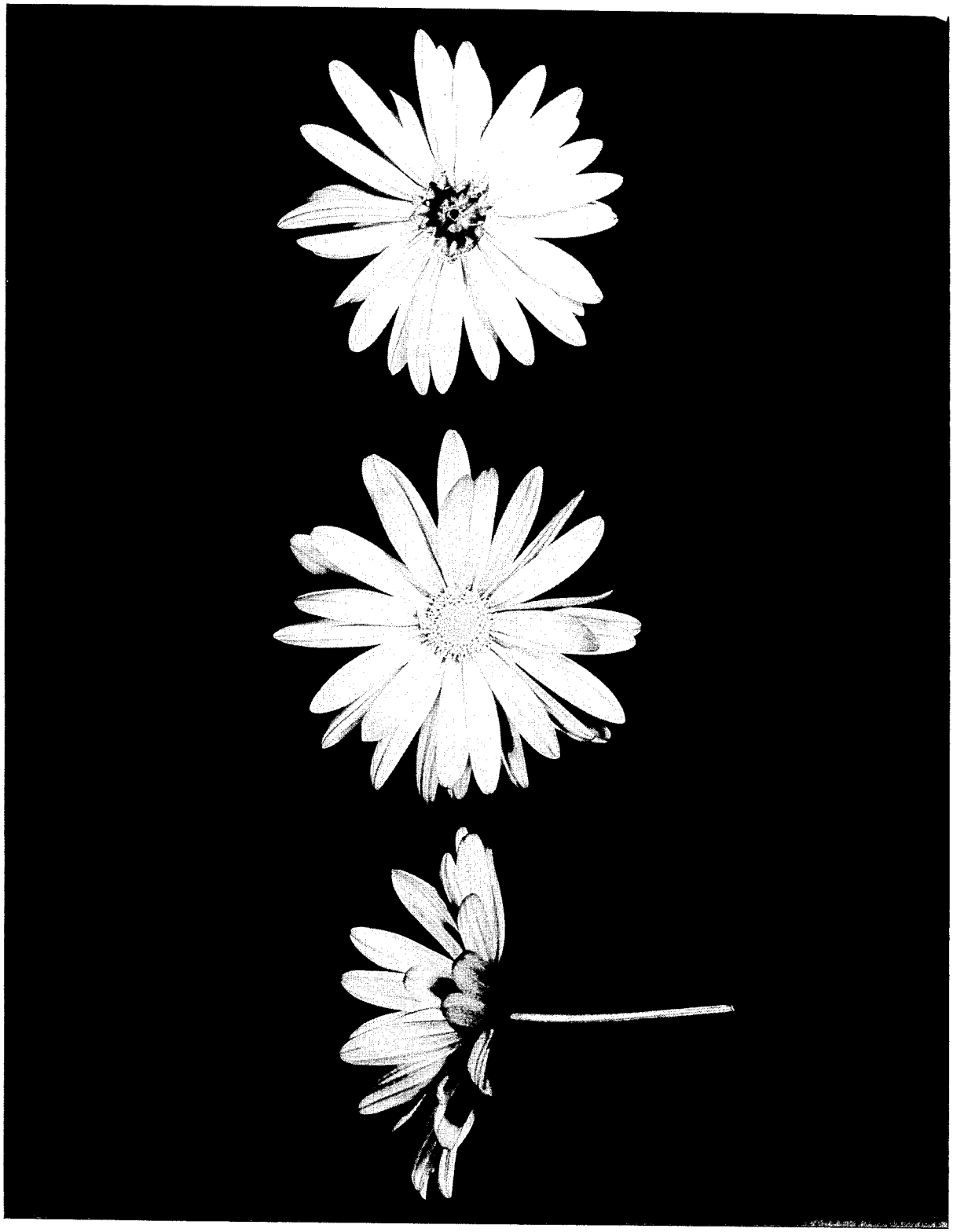

* * * * *